US00PP11479P

United States Patent [19]

van Rijn

[11] Patent Number: Plant 11,479

[45] Date of Patent: Aug. 15, 2000

[54] ANTHURIUM PLANT NAMED 'CORA'

[75] Inventor: Leonardus van Rijn, Schipluiden, Netherlands

[73] Assignee: RijnPlant B.V., Schipluiden, Netherlands

[21] Appl. No.: 09/177,290

[22] Filed: Oct. 22, 1998

[51] Int. Cl.[7] ..... A01H 5/00

[52] U.S. Cl. ..... Plt./365

[58] Field of Search ..... Plt./365, 369

[56] References Cited

U.S. PATENT DOCUMENTS

P.P. 9,080 3/1995 Hope ..... Plt./369

P.P. 9,714 11/1996 Van Rosmalen ..... Plt./369

*Primary Examiner*—Lynette R. F. Smith
*Assistant Examiner*—Kent L. Bell
*Attorney, Agent, or Firm*—C. A. Whealy

[57] ABSTRACT

A distinct cultivar of Anthurium plant named 'Cora', characterized by its upright and outwardly arching growth habit; durable, thick, dark green leaves that are ovate to cordate in shape; numerous inflorescences that are positioned upright and above the foliage on strong and erect scapes; durable thick red spathes; strong rooting system; year-round continuous flowering; and good post-production longevity.

2 Drawing Sheets

BACKGROUND OF THE INVENTION

The present invention relates to a new and distinct cultivar of Anthurium plant, botanically known as *Anthurium andreanum,* and hereinafter referred to by the cultivar name 'Cora'.

The new Anthurium is a product of a planned breeding program conducted by the Inventor in Schipluiden, The Netherlands. The objective of the program is to create new Anthurium cultivars that have a freely clumping growth habit, strong roots and plant growth, attractive spathe color, numerous inflorescences and leaves, and good post-production longevity.

The new Anthurium originated from a cross by the Inventor on Aug. 10, 1991 of the Inventor's proprietary *Anthurium andreanum* selection code number 90-3 as the female, or seed, parent with the Inventor's proprietary *Anthurium andreanum* selection code number 90-6 as the male, or pollen, parent. The cultivar 'Cora' was discovered and selected by the Inventor as a plant within the progeny of the stated cross in a controlled environment in Schipluiden, The Netherlands in September, 1993.

Asexual propagation of the new cultivar by tissue culture in a laboratory in Belgium has shown that the unique features of this new Anthurium plant are stable and reproduced true to type in successive generations of asexual propagation.

BRIEF SUMMARY OF THE INVENTION

The new Anthurium has not been observed under all possible environmental conditions. The phenotype may vary somewhat with variations in environment such as temperature and light intensity, without, however, any variance in genotype.

The following traits have been repeatedly observed and are determined to be the unique characteristics of the cultivar 'Cora'. These characteristics in combination distinguish 'Cora' as a new and distinct cultivar:

1. Upright and outwardly arching growth habit.

2. Durable, thick, dark green leaves that are ovate to cordate in shape.

3. Nurmerous inflorescences that ar positioned upright and above the foliage on strong and erect scapes.

4. Durable thick red spathes.

5. Strong rooting system.

6. Year-round continuous flowering.

7. Good post-production longevity.

The new Anthurium can be compared to the female parent, the Inventor's proprietary selection code number 90-3. In side-by-side comparisons conducted by the Inventor in Schipluiden, The Netherlands, plants of the new Anthurium differ from plants of selection code number 90-3 in the following characteristics:

1. Spathe color of plants of the new Anthurium is red whereas spathe color of plants of the selection code number 90-3 is orange.

2. Plants of the new Anthurium are more compact and less freely clumping than plants of the selection code number 90-3.

3. Plants of the new Anthurium have thicker leaves than plants of the selection code number 90-3.

4. Plants of the new Anthurium have thicker spathes than plants of the selection code number 90-3.

The new Anthurium can be compared to the male parent, the Inventor's proprietary selection code number 90-6. In side-by-side comparisons conducted by the Inventor in Schipluiden, The Netherlands, plants of the new Anthurium differ from plants of selection code number 90-6 in the following characteristics:

1. Spathe color of plants of the new Anthurium is red whereas spathe color of plants of the selection code number 90-6 is pink.

2. Plants of the new Anthurium are less compact and less freely clumping than plants of the selection code number 90-6.

3. Plants of the new Anthurium have thicker leaves than plants of the selection code number 90-6.

4. Plants of the new Anthurium have thicker spathes than plants of the selection code number 90-6.

Compared to plants of the sibling cultivar 'Claudia', disclosed in the U.S. Plant Pat. application Ser. No. 09/177, 594, plants of the new Anthurium are shorter, have smaller leaves and spathes, and have darker red-colored spathes. Compared to plants of the sibling cultivar 'Saskia', disclosed in U.S. Plant Pat. application Ser. No. 09/177,591, plants of the new Anthurium have darker red-colored spathes.

The new Anthurium can be compared to the Anthurium cultivar 'Leny' disclosed in U.S. Plant Pat. No. 10,272. However, in side-by-side comparisons conducted by the Inventor in Schipluiden, The Netherlands, plants of the new Anthurium differ from plants of the cultivar Leny in the following characteristics:

1. Plants of the new Anthurium have darker green, thicker and rougher leaves than plants of the cultivar 'Leny'.

2. Plants of the new Anthurium have thicker and rougher spathes than plants of the cultivar 'Leny'.

BRIEF DESCRITPTION OF THE PHOTOGRAPHS

The accompanying colored photographs illustrate the overall appearance of the new Anthurium, showing the colors as true as it is reasonably possible to obtain in colored reproductions of this type.

The photograph on the first sheet comprises a top perspective view of a typical potted plant of the cultivar 'Cora'.

The photograph on the second sheet comprises a close-up view of a typical spathe and spadix of the cultivar 'Cora'. Leaf, spathe and spadix colors in the photographs may appear lighter than the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe one-year old plants grown in Schipluiden, The Netherlands, in a glass greenhouse with an average day temperature of 25° C. and an average night temperature of 19° C.

Botanical classification: *Anthurium andreanum* cultivar 'Cora'.

Parentage:

*Female parent.*—Inventor's proprietary *Anthurium andreanum* selection code number 90-3.

*Male parent.*—Inventor's proprietary *Anthurium andreanum* selection code number 90-6.

Propagation:

*Method.*—Typically by tissue culture.

*Time to initiate roots.*—About 70 or 84 days at 24° C. or 21° C., respectively.

*Rooting habit.*—Numerous and very strong fleshy roots.

Plant description:

*Plant shape.*—Upright, inverted triangle, symmetrical.

*Growth habit.*—Erect when young, becoming outwardly arching as leaves develop. Appropriate for 17-cm and larger containers.

*Plant height.*—About 50 cm from soil level to apex of spathes.

*Plant vigor.*—High.

*Growth rate.*—Moderate to rapid.

*Crop time.*—About 10 months are usually required from planting of young plants to finished plants in 17-cm containers.

*Foliage description.*—Quantity: Usually about 60 leaves per finished container. Length: About 23.5 cm. Width: About 15 cm. Shape: Ovate to Cordate. Apex: Apiculate to aristate. Base: Auriculate; to cordate; lobes not overlapping. Margin: Entire. Texture: Smooth, glabrous, leathery. Color: Young leaves, upper surface: Brownish red to green. Young leaves, lower surface: Brownish red to green. Mature leaves, upper surface: 137A to 147A. Mature leaves, lower surface: 144A to 146C. Petiole: Length: About 36 cm. Color: 144A to 146B. Geniculum length: About 2.5 cm.

Inflorescence description:

*Inflorescence arrangement.*—Spathe with spadix held above the foliage. Flowering structures arise from leaf axils. Freely flowering; continuous flowering year-round; typically four to seven inflorescences per plant. Not fragrant.

*Inflorescences longevity.*—Infloresces last about six weeks under winter conditions and up to three months under summer conditions; persistent.

*Flowers.*—Quantity per spadix: Numerous, about 150. Shape: Rounded. Diameter: About 1 mm, maximum.

*Spathe.*—Length: About 8 cm. Width: About 8.75 cm. Height above foliage: About 9 cm. Shape: Deltoid. Apex: Apiculate to mucronate. Base: Auriculate to cordate; lobes not overlapping. Margin: Entire. Texture: Leathery, glabrous, slight to medium blistering, shiny. Color: When opening: 45A. Front surface: 46A. Back surface: 45C to 45D. After senescence: 45A to 46A.

*Spadix.*—Length: About 5 cm. Diameter: About 9 mm. Shape: Columnar. Cross section: Rounded. Longitudinal axis: Very weakly recurved to erect. Color: Base: Very pale yellow, 19D. Mid-section: 19D. Apex: 15B. Color, after senescence: Close to 22A.

*Scape.*—Length: About 45 cm. Aspect: Strong and erect. Color: 144A with anthocyanin towards apex.

*Reproductive organs.*—Androecium: Pollen color: Creamy white. Gynoecium: Stigma shape: Ovoid.

Disease resistance: Plants of the new Anthurium have not been shown to be resistant to disease common to Anthurium.

Seed development: Seed developoment of the new Anthurium has not been observed.

It is claimed:

1. A new and distinct cultivar of Anthurium plant named 'Cora', as illustrated and described.

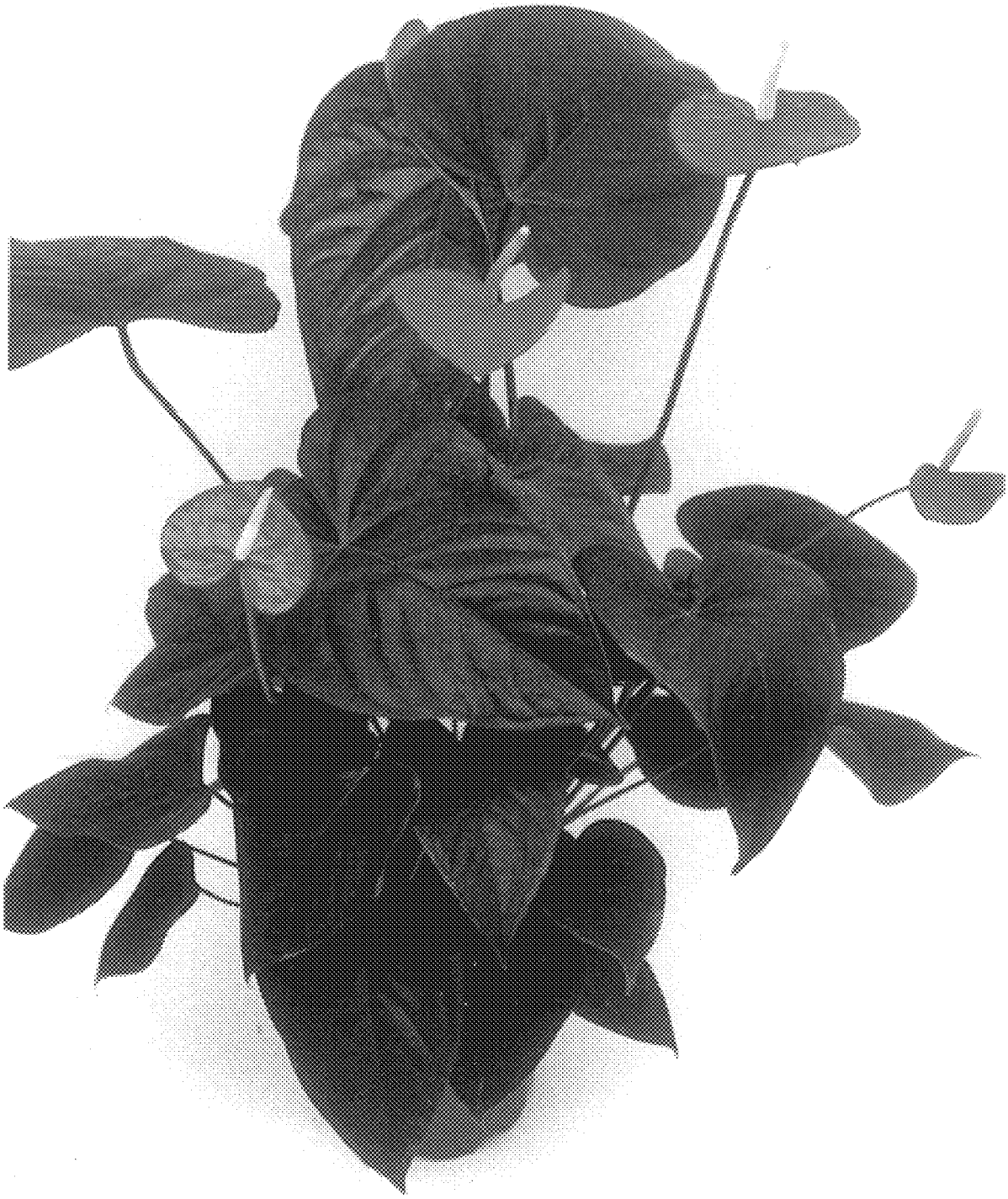

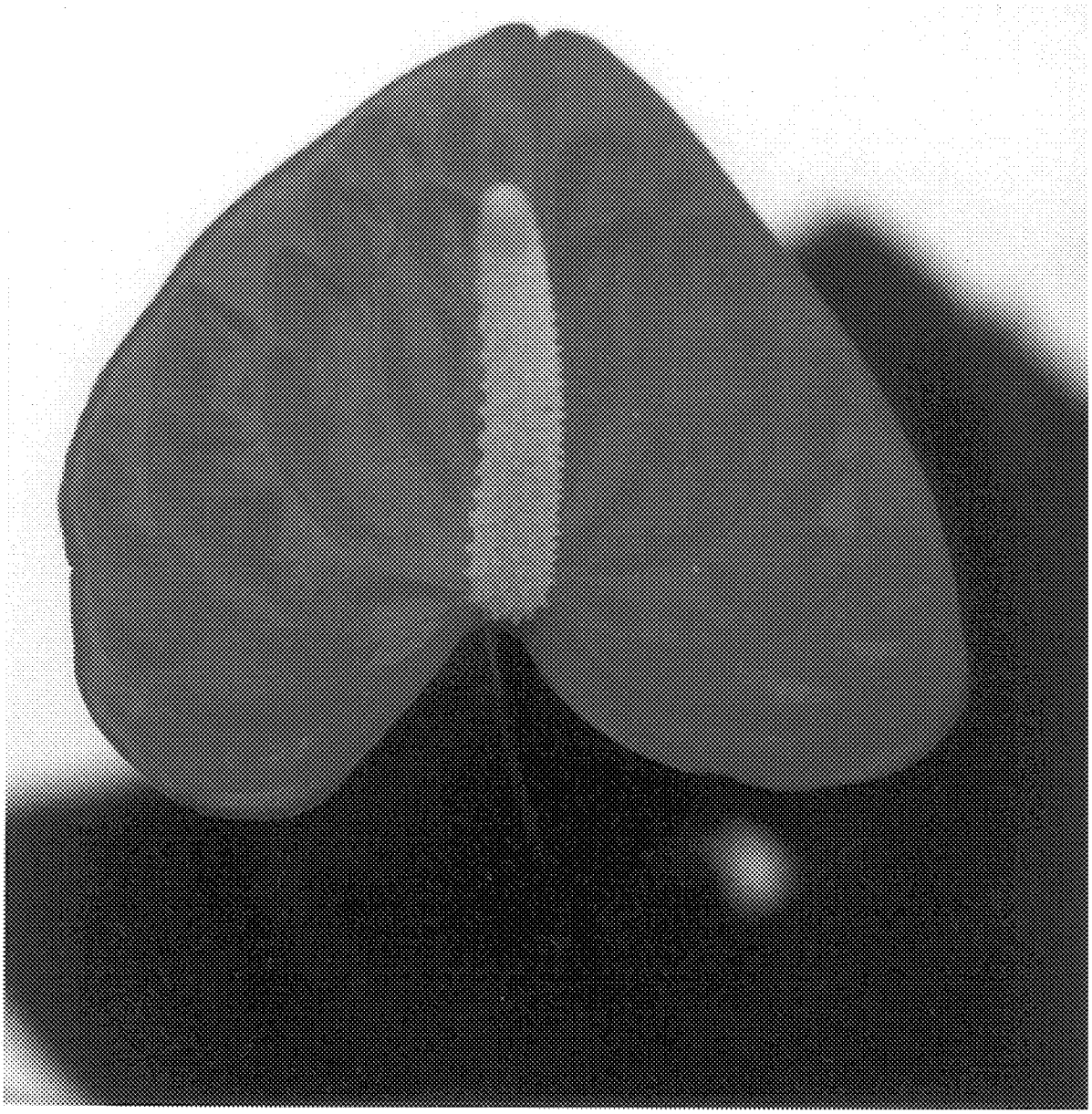

* * * * *